United States Patent [19]

Schlosberg

[11] 4,326,949

[45] Apr. 27, 1982

[54] OXYGEN ALKYLATION OF PHENOL-CONTAINING HYDROCARBONACEOUS STREAMS

[75] Inventor: Richard H. Schlosberg, New Providence, N.J.

[73] Assignee: Exxon Research & Engineering Co., Florham Park, N.J.

[21] Appl. No.: 200,515

[22] Filed: Oct. 24, 1980

[51] Int. Cl.³ .................. C07C 37/68; C10G 17/00
[52] U.S. Cl. ..................... 208/263; 568/630; 568/749; 568/761
[58] Field of Search .................. 208/263; 568/630

[56] References Cited

U.S. PATENT DOCUMENTS

| | | | |
|---|---|---|---|
| 2,059,075 | 10/1936 | Yabroff et al. | 208/263 |
| 2,256,612 | 9/1941 | Ellis | 568/630 |
| 3,359,197 | 12/1967 | Masciantonio et al. | 208/14 |
| 3,376,212 | 4/1968 | Masciantonio et al. | 208/14 |
| 3,992,432 | 11/1976 | Napier et al. | 260/465.1 |
| 4,256,568 | 3/1981 | Schlosberg et al. | 208/263 |
| 4,259,172 | 3/1981 | Liotta | 208/14 |

FOREIGN PATENT DOCUMENTS 851191 5/1977 Belgium.
2634419 10/1977 Fed. Rep. of Germany.

OTHER PUBLICATIONS

Lahiri et al., J. Sc. Ind. Res. (India), vol. 18B, pp. 492–493 (1959).
Zabavin, Bul. Ac. Sc., USSR, Classe Sci., Tech., No. 8, pp. 35–49 (1943).
Danetskaya, Gigiena i Sanit., pp. 26–31 (1952).
Brändström et al., Acta Chem., vol. 23, p. 2202 (1969).
Wagenknecht et al., Synthetic Communications, vol. 2, pp. 215–219 (1972).
Bashall et al., Tetrahedron Letters, pp. 3489–3490 (1975).
Hodek et al., FUEL, vol. 52, pp. 220–225 (1973).
Olleman, Anal. Chem., vol. 24, pp. 1425–1439 (1952).
Lahiri et al., FUEL, vo. 36, pp. 254–256 (1957).
Lahiri et al., J. Indian Chem. Soc., Ind. & News Ed., vol. 20, pp. 91–94 (1957).
Heathcoat et al., J.C.S., 1932, pp. 2839–2843.
Kroger et al., Erdöl und Kohle Erdgas Petrochemie, vol. 18, pp. 368–372 (1965).
Sokolova et al., Trudy Inst. Nefti, Akad. Nauk SSSR, vol. 1, pp. 277–284 (1950).
Fugassi et al., A.C.S., Div. Gas Fuel Chem., Preprints, pp. 125–131.
Eckhard et al., Tetrahedron Letters, pp. 95–96 (1976).
Blom et al., FUEL, vol. 36, pp. 135–153 (1957).
Yohe et al., J.A.C.S., vol. 69, pp. 2644–2648 (1947).
Sternberg et al., FUEL, vol. 53, pp. 172–175 (1974).
McKillop et al., "The Synthesis of Phenol Ethers", Tetrahedron, vol. 30, pp. 1379–1382 (1974).
Eastman Organic Chemical Bulletin, vol. 48, No. 1 (1976).

*Primary Examiner*—Delbert E. Gantz
*Assistant Examiner*—Olik Chaudhuri
*Attorney, Agent, or Firm*—Henry E. Naylor

[57] ABSTRACT

A method for separating phenols from phenol-containing streams and converting them to ethers by: (a) contacting the phenol-containing stream with a multivalent metal composition capable of forming hydroxy metal phenates with the phenols from the stream; (b) separating the hydroxy metal phenate from the stream; and (c) reacting the hydroxy metal phenate with one or more quaternary Group VA compounds represented by the formula $R_3R'MOR''$ or $R_3R'MX$.

38 Claims, No Drawings

OXYGEN ALKYLATION OF PHENOL-CONTAINING HYDROCARBONACEOUS STREAMS

BACKGROUND OF THE INVENTION

The present invention relates to the separation of phenols from phenol-containing streams and converting them to ethers by use of one or more multivalent metal oxides and/or hydroxides, whereupon the resulting hydroxy metal-phenate is reacted with a quaternary ammonium or phosphonium salt or base.

The presence of phenols in various hydrocarbonaceous streams is troublesome. For example, the presence of phenol functionality in liquids produced from coal causes instability of these liquids over a period of time by increasing the viscosity, the color intensity, and causing separation of resinous materials. Moreover, without extensive hydrotreatment, coal liquids are generally not compatible with petroleum liquids of comparable boiling point. Thus, solids separation caused largely by high concentrations of phenols leads to severe operability problems for coal/petroleum liquid blends. Also, hydrodesulfurization and hydrodenitrogenation of coal liquids are required prior to reforming into gasoline. These steps generally require substantial consumption of hydrogen for phenol-rich coal liquids because of the extensive deoxygenation of phenols to water.

Various methods of separating these troublesome phenols from hydrocarbonaceous streams are taught in the art. For example, it is taught that weakly acidic organic substances such as phenols can be removed from hydrocarbonaceous streams by use of alkali metal or alkaline-earth metal oxides or hydroxides. It is also taught that the phenols react with these oxides or hydroxides resulting in this formation of phenoxide salts which can be easily separated from the purified stream. Further, it is known that certain phenoxide salts, such as calcium phenoxide, can be heated in the presence of carbon dioxide to yield phenols and calcium carbonate.

Another method taught for separating phenols from hydrocarbonaceous streams is to wash the stream with large quantities of water or aqueous caustic solutions such as sodium or potassium hydroxide.

Although such methods are practiced on a commercial scale in various industries, there is still a need to develop a process for removing, from hydrocarbonaceous streams, troublesome phenols, recovering the phenols in a more efficient and inexpensive way and converting the phenols to more non-polar species which would be more compatible with petroleum liquids.

SUMMARY OF THE INVENTION

In accordance with the present invention a method is provided for separating phenols from phenol-containing hydrocarbonaceous streams and converting them to ethers. The method comprises (a) contacting the phenol-containing stream with a multivalent metal composition selected from the group consisting of one or more oxides and/or hydroxides of multivalent metals capable of forming hydroxy metal phenates with the phenols of the stream, wherein the stream is contacted at a temperature below the decomposition temperature of the hydroxy metal-phenate; (b) separating the hydroxy metal phenate from the stream; and (c) reacting the hydroxy metal-phenate with one or more quaternary Group VA bases represented by the formula $R_3R'MOR''$ or one or more quaternary Group VA halides represented by the formula $R_3R'MX$ where each R is the same or different group selected from the $C_1$ to about $C_{20}$ alkyl, aryl, acyl, arylalkyl, alkylaryl, ether and ester groups, sulfide, amine and heteroatoms of silicon, selenium or a metal selected from Groups I and II of the Periodic Table of the Elements. R' is a $C_1$ to $C_4$ alkyl group. M is an element selected from Group VA of the Periodic Table of the Elements. R'' is hydrogen, or a $C_1$ to about $C_{20}$, alkyl, aryl, arylalkyl or alkylaryl group. O is oxygen and X is a halide selected from the group consisting of iodine, bromine and chlorine.

In one preferred embodiment of the present invention the phenol-containing carbonaceous stream is a coal liquid, the multivalent metal composition is calcium oxide or calcium hydroxide, and the quaternary compound is a halide selected from the group consisting of the $C_1$ to $C_4$ quaternary ammonium halides.

In another preferred embodiment of the present invention, the quaternary compound is a base selected from the group consisting of the $C_1$ to $C_4$ quaternary ammonium hydroxides.

DETAILED DESCRIPTION OF THE INVENTION

Phenol-containing hydrocarbonaceous streams which can be treated according to this invention include, but are not limited to, those streams resulting from the processing of coal, petroleum, and those existing as impurities in such parent streams as linear paraffins.

The term phenol-containing hydrocarbonaceous stream means a hydrocarbonaceous stream containing measurable amounts of phenol compounds in which one or more hydroxyl groups are attached to an aromatic ring and where the aromatic ring may also contain a heteroatom (e.g. nitrogen in a pyridine ring). Non-limiting examples of such phenol compounds include phenol itself (also known as benzophenol), the cresols, xylenols, resorcinol, naphthols, 8-hydroxyquinoline, and 4-hydroxyquinoline. The phenol-containing hydrocarbonaceous stream, exclusive of the phenol compounds, also contains at least 25 wt. % of compounds containing carbon and hydrogen, though other atoms (e.g. nitrogen, oxygen, sulfur) may also be present.

The present invention is not dependent on the method of producing the phenol-containing hydrocarbonaceous stream. For example, any coal liquid containing phenols can be treated regardless of its method of production. Non-limiting examples of processes for producing coal liquids include pyrolysis, solvent refining, direct hydrogenation with or without a catalyst, catalytic or non-catalytic hydrogenation in the presence of a non-hydrogen donor solvent and catalytic or non-catalytic liquefaction in the presence of a hydrogen donor solvent.

Although not wishing to be limited hereby, one preferred method for obtaining coal-liquids is the Exxon Donor Solvent (EDS) process for the liquefaction of coal and described in U.S. Pat. No. 3,617,513 incorporated herein by reference. Briefly stated, the EDS process involves the formation of a slurry of coal in a hydrogen-donor solvent, such as tetralin, maintained at elevated temperatures of about 260° C. to 370° C. under agitation. Holding the coal at these temperatures causes the coal to disintegrate and dissolve without the breaking of a significant number of coal covalent bonds thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking or depolymerization temperatures above about 370° C. under a pressure effective to maintain the dispersant slurry substantially in the liquid phase, generally about 350 p.s.i.g. to 3500 p.s.i.g. In this second temperature stage, the dissolved coal particles are well dispersed in the hydrogen-donor solvent and the chance of a hydrogen-donor stabilization of free radicals generated by bond breaking is maximized. At the same time, the chance for free radicals to combine with one another to produce undesirable molecules is minimized. The dispersed slurry is maintained at the elevated temperatures above about 370° C. until a predetermined conversion of the coal is obtained. The liquid, which contains phenols, is then distilled and hydrogenated, the gases drawn off, and the bottoms removed for coking and gasification.

In accordance with the present invention, the phenol-containing stream is treated with one or more multivalent metal oxides and/or hydroxides capable of forming a hydroxy metal phenate with the phenols of the stream. The stream is contacted at a temperature below the decomposition temperature of the resulting hydroxy metal phenate; generally from about room temperature (25° C.) to the decomposition temperature of the hydroxy metal phenate. For example, when calcium is the multivalent metal of the oxides and/or hydroxides used herein, the decomposition temperature of its resulting hydroxy calcium phenate is about 490° C. The decomposition temperature of any resulting hydroxy metal phenate can be easily determined by one having ordinary skill in the art and will not be discussed in further detail.

The amount of multivalent metal composition needed in the practice of the invention is dependent on the amount of multivalent metal required to react with a predetermined amount of the phenols in the stream. Although it may be desirable to remove as much of the phenols from the stream as possible, one may only wish to remove a certain minimum amount based on economic considerations.

The concentration of phenols in the hydrocarbonaceous stream can be determined by conventional analytical methods, such as non-aqueous titration. The amount of multivalent metal needed to remove a predetermined amount of phenols can be expressed as the mol ratio of metal (in the oxide and/or hydroxide) to phenolic-oxygen (in the feed stream). The preferred mol ratio of metal to phenolic-oxygen needed herein is that ratio which, when the metal oxides and/or hydroxides are contacted with the stream, will assure the removal of at least about 15 wt. % of the phenols from the feed stream at a temperature of about 25° C. for a contact time of about 90 minutes. The wt. % of phenol removal is based on the total weight of phenols in the stream.

It will be noted that because the activity of some metals is greater than that of other metals under a given set of conditions, less of the more active metal, for a given amount of phenols in the feed stream is required to remove a predetermined amount of the phenols from the stream. For example, at a temperature of 25° C. and a contact time of 90 minutes, 17 wt. % of phenols are removed from a phenol-containing coal liquid using zinc hydroxide at a metal to oxygen mol ratio of 1.0 whereas at the same temperature and metal to oxygen mol ratio, about 72 wt. % of phenols are removed from the same coal liquid when calcium hydroxide is used. The relative activity of one metal to another is known in the art and the ratio of any given metal to oxygen can be determined by routine experimentation or calculation by one having ordinary skill in the art.

In order to achieve a high percentage of phenol removal with any metal, a multistage process can be used. For example, at a calcium to oxygen mol ratio of 0.2, a contact time of 90 minutes, and at a temperature of 25° C., 48 wt. % removal of phenols from a coal liquid is achieved. If the treated coal liquid is contacted a second time under the same mole ratio, time, and temperature conditions as the first stage, an overall 77 wt. % removal of phenols is achieved. Therefore, it may be desirable to contact the liquid from a previous stage many times over to effect substantially total removal of the phenols from the stream. For example, after initial contact of the stream with the multivalent metal composition, the treated stream is separated from the resulting hydroxy metal phenate and passed on to another stage for contact with additional multivalent metal composition. This sequence can be repeated as often as practical and desirable.

It may be desirable from an energy savings point of view to contact the phenol-containing hydrocarbonaceous stream at elevated temperatures with the multivalent metal composition. In this context, elevated temperatures means temperatures greater than room temperature but lower than the decomposition temperature of the resulting hydroxy metal phenate. Generally, the phenol-containing feed stream will result from a chemical, petroleum, or coal process and will exit such process at elevated temperatures whereupon it can be treated directly with the multivalent metal composition as long as the temperature of the stream is lower than the decomposition temperature of the resulting hydroxy metal phenate. Therefore, the temperature of the phenol-containing feed stream is dependent on the source, and process for its production, and may have to be cooled to a lower temperature before treatment.

Preferably, it is desirable to treat the feed stream with the multivalent metal composition as close to a desired temperature for ether formation as possible. By doing so, the rate of reaction is increased and the addition of heat is not required to bring the feed stream up to an efficient reaction temperature. Therefore, if the feed stream exits a previous process already at elevated temperatures, and is treated according to the invention at those temperatures, an energy savings is realized because no external heat is needed for elevating the temperature of the feed stream to a more desirable reaction temperature.

Although not wishing to be limited by theory, it is believed that the multivalent metals suitable for use herein form a hydroxy metal phenate with the phenol compounds of the hydrocarbonaceous stream. These hydroxy metal phenates can then be reacted at temperatures from about 100° C. to 350° C. with the quaternary halide or base. The following is illustrative of the reaction scheme which is believed to occur when the metal composition is calcium hydroxide and the quaternary compound is a quaternary ammonium hydroxide.

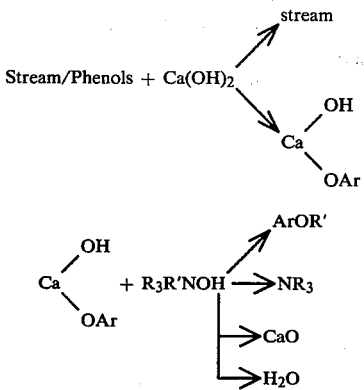

According to the above, the reaction of the calcium hydroxy phenate with the quaternary ammonium hydroxide results in the following products: (a) an ether ArOR', (2) a trisubstituted amine $NR_3$, (3) calcium oxide CaO, and (4) water.

The resulting metal oxide, calcium oxide, can be recycled directly or it can be hydrolyzed by any conventional means, preferably by the introduction of stoichiometric amounts of water to convert the oxides to their corresponding preferred hydroxides.

When the quaternary compound is a quaternary ammonium halide and the metal composition is calcium hydroxide, the following reaction scheme is believed to be representative:

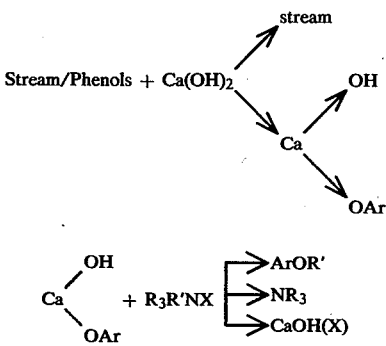

The above reaction scheme shows that the reaction of the calcium hydroxy phenate with the quaternary ammonium halide results in the following products: (1) an ether ArOR', (2) a trisubstituted amine $NR_3$, and (3) an inorganic phase represented by the stoichiometry CaOH(X). This CaOH(X) phase can be heated to generate CaO plus HX. The CaO can be recycled directly or hydrolyzed as indicated above. The HX can be recycled and used to prepare R'X for the reaction with $R_3N$ to make $R_3R'NX$.

In the above reaction schemes, the groups are as previously indicated herein. It is preferred that the transferring group R' be such that the volatility of the resulting ether be substantially the same as the phenol from which it is produced. Therefore, for most practical purposes, it is preferred that the R' group be a $C_1$ to $C_6$ alkyl group.

The trisubstituted amine, $NR_3$, can be treated to regenerate the quaternary base by conventional techniques. One technique, which can be employed, is alkylation of the trisubstituted amine with an alkylating agent to form a quaternary salt. This salt can be used as is or it can be converted to the corresponding quaternary hydroxide by treatment with silver oxide. Other conventional techniques include electrolysis and an ion-exchange method in which the quaternary salt solution is passed through an iron-exchange column filled with a highly basic anion-exchange resin, preferably in —OH form. Such resins are generally known in the art and the selection of any particular resin, as well as the reaction conditions, can be determined by routine experimentation by one having ordinary skill in the art.

The quaternary compound can be reacted with the hydroxy metal phenate in various ways. For example, when the quaternary compound employed is a salt, it can be employed in solid form or put into solution to form the corresponding base. If employed in solid form, the quaternary salt is mixed with the hydroxy metal phenate and heated to approximately the melting point of the quaternary salt. The quaternary salt may also be employed in solution form by dissolving it with an appropriate solvent. Such solvents include the dipolar and aprotic solvents selected from the group consisting of: N,N-dimethyl-formamide (DMF); N,N-dimethylacetamide (DMAC); N,N,N,N-tetramethylurea (TMU); N-methylpryllidone (NMP); and the like, as well as mixtures thereof.

Non-limiting examples of preferred quaternary bases suitable for use herein include tetramethylammonium hydroxide and alkoxide, tetraethylammonium hydroxide and alkoxide, tetrapropylammonium hydroxide and alkoxide, tetrabutylammonium hydroxide and alkoxide, tetrapentylammonium hydroxide and alkoxide, tetrahexylammonium hydroxide and alkoxide, benzylhexadecyldimethyl ammonium hydroxide and alkoxide, tetraethylphosphonium hydroxide and alkoxide, tetrapropylphosphonium hydroxide and alkoxide, tetrabutylphosphonium hydroxide and alkoxide, tetraphenyl, phosphonium hydroxide and alkoxide, tetrahexylphosphonium hydroxide and alkoxide, and benzylhexadecyldimethylphosphonium hydroxide and alkoxide, as well as similar bases having different alkyl groups such as triethylmethyl ammonium hydroxide and alkoxide and the like. Preferred are the ammonium hydroxides and $C_1$ to $C_4$ alkoxides, more preferred are the ammonium hydroxides, and most preferred is tetramethyl ammonium hydroxide.

Non-limiting examples of preferred quaternary halides suitable for use herein include tetramethyl ammonium iodide, bromide, and chloride; tetraethylammonium iodide, bromide and chloride; tetrapropylammonium iodide, bromide and chloride; tetrabutylammonium iodide, bromide and chloride; tetrapentylammonium iodide, bromide and chloride, tetrahexylammonium iodide, bromide and chloride; as well as similar halides having mixed alkyl groups such as triethylmethylammonium iodide, bromide and chloride, and the like.

The following examples serve to more fully describe the manner of practicing the above-described invention, as well as to set forth the best modes contemplated for carrying out various aspects of the invention. It is understood that these examples in no way serve to limit the true scope of this invention, but rather are presented for illustrative purposes.

EXAMPLES 1–4

Various multivalent metal oxides were used to extract phenols from a phenol-containing naptha cut derived from a coal liquefaction process. The naphtha cut contained 1 mmol of oxygen/gm of naphtha, which oxygen is essentially all present as phenols. Concentrations of oxides were used to give a mol ratio of metal in the oxide to phenolic-oxygen in the naphtha cut of 1.0. The naphtha cut in each instance was contacted for 90 minutes with the multivalent metal oxide at a temperature of 25° C. A hydroxy metal phenate resulted and was separated from the treated naphtha cut. The amount of phenols removed was determined by gas chromatography wherein the phenol content of the non-treated naphtha was compared to that of the treated naphtha. The results are set forth in Table I below:

TABLE I

| Effect of Metal Atom on Removal of Phenols When Used in Oxide Form | | |
|---|---|---|
| Ex | Metal Ion | Wt. % Phenol Removal |
| 1 | $Ca^{++}$ | 49 |
| 2 | $Sr^{++}$ | 65 |
| 3 | $Ba^{++}$ | 100 |
| 4 | $Ni^{+++}$ | 25 |

The above table shows that at a mol ratio of metal to phenolic-oxygen of 1, at a temperature of 25° C. and for a contact time of 90 minutes, the oxides of Ca, Sr, Ba and $Ni^{3+}$ are able to remove at least 25 wt. % of the phenols from the phenol-containing naphtha stream. The weight percent of phenol removed is based on the total weight of phenols in the untreated naphtha stream.

COMPARATIVE EXAMPLES A-D

For comparative purposes, various multivalent metal oxides, other than those of Examples 1-4, were used according to the conditions set forth in Examples 1-4. The results are shown in Table II below:

TABLE II

| Effect of Metal Atom on Removal of Phenol When Used in Oxide Form | | |
|---|---|---|
| Ex | Metal Ion | Wt. % Phenol Removal |
| A | $Mg^{++}$ | 5 |
| B | $Zn^{++}$ | 9.8 |
| C | $Ni^{++}$ | 9 |
| D | $Ce^{4+}$ | 3 |

The above table shows that not all multivalent metal oxides are capable of removing at least 15 wt. % of phenols from the untreated naphtha cut.

EXAMPLES 5-10

Various multivalent metal oxides were used to remove phenols from the same naphtha cut and under the same conditions set forth in Examples 1-4 except, a stoichiometric amount of water was added to completely (hydrate) convert the metal oxide to the corresponding hydroxide. The results are set forth in Table III below.

TABLE III

| Effect of Metal Atom on Removal of Phenols When Used in Hydroxide Form | | |
|---|---|---|
| Ex | Metal Ion | Wt. % Phenol Removal |
| 5 | $Ca^{++}$ | 72 |
| 6 | $Sr^{++}$ | 99 |
| 7 | $Ba^{++}$ | 100 |
| 8 | $Zn^{++}$ | 17 |
| 9 | $Ni^{++}$ | 15 |
| 10 | $Ni^{+++}$ | 33 |

Table III shows, that generally, the multivalent metal hydroxide is preferred over the corresponding oxide because of its increased phenol removal capabilities Although when barium is the multivalent metal, substantially all of the phenols are removed with either the oxide or hydroxide form.

COMPARATIVE EXAMPLE E

Comparative example D was repeated except a stoichiometric amount of water was added to completely (hydrate) convert cerium oxide to cerium hydroxide during phenol removal. After analysis by gas chromatography, it was found that the amount of phenol removal for cerium hydroxide was 7 wt. % vs. 3 wt. % for the corresponding oxide. This shows that even the hydroxide form of some multivalent metals is incapable of removing at least 15 wt. % of the phenols from a phenol-containing naphtha stream.

EXAMPLES 11-18

Various mol ratios of calcium, in its hydroxide form, to oxygen, in the naphtha cut, were used to remove phenols from the naphtha stream of Examples 1-4. These runs were performed at 25° C. for a 90 minute contact time in either 1 or 2 stage processes as indicated below. That is, if the process was a two stage process, the naphtha stream (treated or untreated depending on the stage) was contacted with calcium hydroxide for 90 minutes in each stage. The results are set forth in Table IV below:

TABLE IV

| Comparison of Removal Efficiencies for 1 and 2 Stage Batch Processes at Various M/O Values | | | |
|---|---|---|---|
| Ex | M/O Ratio | # of Stages | Wt. % Phenol Removal$^{(a)}$ |
| 11 | 0.1 | 1 | 32 |
| 12 | 0.1 | 2 | 54 |
| 13 | 0.2 | 1 | 48 |
| 14 | 0.2 | 2 | 77 |
| 15 | 0.4 | 1 | 61 |
| 16 | 0.4 | 2 | 81 |
| 17 | 0.8 | 1 | 70 |
| 18 | 0.8 | 2 | |

This table shows the advantage of using more than one stage for removal of phenols from a phenol-containing naphtha stream. For example, a two stage process using a specific M/O value for each stage is capable of removing more of the phenols than a one stage process using an M/O value double that of the corresponding two stage process under the same conditions.

EXAMPLE 19

1.5 g (0.01 mol) of hydroxy calcium phenate and 9.0 g of tetrabutyl ammonium chloride (0.032 mol) were mixed in a 128 cc autoclave and sealed under an atmosphere of nitrogen. The reactor was heated to 200° C. for 3 hours (max. pressure=120 psia, final pressure=0). A liquid product was recovered and was found to be comprised of butyl phenyl ether, tributyl amine, and phenol (minor) after analysis by gas chromatography and mass spec. The solid residue was dried for 16 hours at 60° C. under ½ atmosphere, $N_2$ and was found to weigh 0.47 g and was found to be CaO. Theoretical yield for CaO is 0.56 g.

COMPARATIVE EXAMPLE 1.5 g of hydroxy calcium phenate and 3.0 g of tetrabutyl ammonium chloride (0.011 mol) were mixed in a 128 cc autoclave and sealed under an atmosphere of nitrogen. The reactor was heated to 100° C. for 1 hour. The product, which was taken up in DMF was found to be phenol only.

EXAMPLE 20

Example 1 was repeated at 100° C. for two hours. Only minor amounts of phenyl butyl ether were found.

EXAMPLE 21

2.88 g of raw coal naphtha containing about 10 wt. % phenols (phenol and cresols) and 5.0 g of calcium hydroxide was agitated for 24 hours at room temperature. 12.2 g of solid material resulted. Infrared analysis of the remaining naphtha showed the absence of —O—H groups and thermal gravimetric analysis (TGA) of the resulting solid indicated a minor weight loss at 122° C. and major weight loss at 520° C. The major weight loss at 520° C. evidences that the resulting solid was comprised of calcium hydroxy phenates. The small weight loss at 122° C. represented adsorbed phenols.

EXAMPLE 22

1.5 g (0.008 mol) of hydroxy calcium phenates derived from raw coal naphtha containing about 10 wt. % phenols (phenol and cresols) and 8.0 g (0.033 mol) of tetrabutyl ammonium chloride were mixed in a 128 cc autoclave and sealed under an atmosphere of nitrogen. The reactor was heated for 2.75 hours at 200° C. The resulting liquid was analyzed and was found to contain tributyl amine, butyl phenyl ether, and butyl tolyl ethers

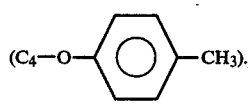

EXAMPLE 23

1.5 g hydroxy calcium phenate and 19.6 g (0.03 mol) of a 40% aqueous solution of tetrabutyl ammonium hydroxide were mixed in a 128 cc autoclave and sealed under an atmosphere of nitrogen. The reactor was heated for three hours at 250° C. The resulting liquid product was taken up in ether and was found to contain butyl phenyl ether.

What is claimed is:

1. A method for separating phenols from a phenol-containing coal liquid stream and converting the phenols to ethers, the method which comprises:
   (a) contacting the phenol-containing coal liquid stream with one or more oxides and/or hydroxides of multivalent metals capable of forming hydroxy metal phenate with the phenols of the stream, and wherein the contacting is performed at temperatures lower than the decomposition temperature of the hydroxy metal phenates;
   (b) separating the hydroxy metal phenates from the stream; and
   (c) reacting the hydroxy metal phenates with a quaternary compound represented by the formula $R_3R'MOR''$ or $R_3R'MX$ where each R is the same or different group selected from the $C_1$ to about $C_{20}$ alkyl, aryl, acyl, arylalkyl, alkylaryl, ether and ester groups, sulfide, amine and heteroatoms of silicon, selenium or a metal selected from Groups I and II of the Periodic Table of the Elements; R' is a $C_1$ to $C_4$ alkyl group; M is selected from the Group VA of the Periodic Table of the Elements; R'' is hydrogen, or a $C_1$ to about $C_{20}$ alkyl, aryl, arylalkyl, alkylaryl group; and X is a halide selected from the group consisting of iodine, bromine or chlorine.

2. The method of claim 1 wherein the mol ratio of multivalent metal to phenolic oxygen in the stream is such that at least 15 wt. % of the phenols are removed from the stream.

3. The method of claim 1 wherein the multivalent metal is selected from the group consisting of Ca, Ba, Sr and $Ni^{+++}$.

4. The method of claim 2 wherein the multivalent metal is selected from the group consisting of Ca, Ba, Sr and $Ni^{+++}$.

5. The method of claim 4 wherein one or more multivalent metal hydroxides are employed.

6. The method of claim 5 wherein calcium hydroxide is employed.

7. The method of claim 1 wherein the method is continuous and the resulting multivalent metal oxides and/or hydroxides are recycled to the coal liquid feed stream.

8. The method of claim 1 wherein the stream contains a stoichiometric amount of water to hydrolyze any resulting multivalent oxides to hydroxides.

9. The method of claim 1 wherein the quaternary compound is a base and R'' is a $C_1$ to $C_4$ alkyl group or hydrogen.

10. The method of claim 9 wherein R'' is hydrogen.

11. The method of claim 6 wherein R'' is hydrogen.

12. The method of claim 1 wherein M is nitrogen.

13. The method of claim 11 wherein M is nitrogen.

14. The method of claim 1 wherein each R is the same or different $C_1$ to $C_6$ alkyl group.

15. The method of claim 13 wherein each R is the same or different $C_1$ to $C_6$ alkyl group.

16. The method of claim 1 wherein X is chlorine and R' is a methyl group.

17. The method of claim 15 wherein R' is a methyl group.

18. The method of claim 1 wherein the amount of quaternary compound ranges from about a stoichiometric amount to about 10 times the total number of phenolic sites of the coal liquid.

19. The method of claim 17 wherein the amount of quaternary compound ranges from about a stoichiometric amount to about 10 times the total number of phenolic sites of the coal liquid.

20. A method for separating phenols from a phenol-containing hydrocarbonaceous stream and converting the phenols to ethers, the method which comprises:
   (a) contacting the phenol-containing stream with one or more oxides and/or hydroxides of multivalent metals capable of forming hydroxy metal phenates with the phenols of the stream, and wherein the contacting is performed at temperatures lower than the decomposition temperature of the hydroxy metal phenates;
   (b) separating the hydroxy metal phenates from the stream; and
   (c) reacting the hydroxy metal phenates with a quaternary compound represented by the formula $R_3R'MOR''$ or $R_3R'MX$ where each R is the same or different group selected from the $C_1$ to about $C_{20}$ alkyl, aryl, acyl, arylalkyl, alkylaryl, ether and ester groups, sulfide, amine and heteroatoms of silicon, selenium or a metal selected from Groups I and II of the Periodic Table of the Elements; R' is a $C_1$ to $C_4$ alkyl group; M is selected from Group VA of the Periodic Table of the Elements; R" is hydrogen, or a $C_1$ to about $C_{20}$ alkyl, aryl, arylalkyl, alkylaryl group; and X is a halide selected from the group consisting of iodine, bromine or chlorine.

21. The method of claim 20 wherein the mol ratio of multivalent metal to phenolic oxygen in the stream is such that at least 15 wt. % of the phenols are removed from the stream.

22. The method of claim 20 wherein the multivalent metal is selected from the group consisting of Ca, Ba, Sr and $Ni^{+++}$.

23. The method of claim 21 wherein the multivalent metal is selected from the group consisting of Ca, Ba, Sr and $Ni^{+++}$.

24. The method of claim 23 wherein one or more multivalent metal hydroxides are employed.

25. The method of claim 24 wherein calcium hydroxide is employed.

26. The method of claim 20 wherein the method is continuous and the resulting multivalent metal oxides and/or hydroxides are recycled to the hydrocarbonaceous feed stream.

27. The method of claim 20 wherein the stream contains a stoichiometric amount of water to hydrolyze any resulting multivalent oxides to hydroxides.

28. The method of claim 20 wherein the quaternary compound is a base and R" is a $C_1$ to $C_4$ alkyl group or hydrogen.

29. The method of claim 28 wherein R" is hydrogen.

30. The method of claim 25 wherein R" is hydrogen.

31. The method of claim 20 wherein M is nitrogen.

32. The method of claim 30 wherein M is nitrogen.

33. The method of claim 20 wherein each R is the same or different $C_1$ to $C_6$ alkyl group.

34. The method of claim 32 wherein each R is the same or different $C_1$ to $C_6$ alkyl group.

35. The method of claim 20 wherein X is chlorine and R' is a methyl group.

36. The method of claim 34 wherein R' is a methyl group.

37. The method of claim 20 wherein the amount of quaternary compound ranges from about a stoichiometric amount to about 10 times the total number of phenolic sites of the hydrocarbonaceous stream.

38. The method of claim 36 wherein the amount of quaternary compound ranges from about a stoichiometric amount to about 10 times the total number of phenolic sites of the hydrocarbonaceous stream.

* * * * *